(12) United States Patent
Bartholomeusz (10) Patent No.: US 12,186,016 B2
(45) Date of Patent: Jan. 7, 2025

(54) THREE-DIMENSIONAL LASER SCAN FOR FRACTIONAL INJURY

(71) Applicant: Lutronic Corporation, Gyeonggi-do (KR)

(72) Inventor: James Bartholomeusz, Beverly Hills, CA (US)

(73) Assignee: Lutronic Corporation, Gyeonggi-do (KR)

( * ) Notice: Subject to any disclaimer, the term of this patent is extended or adjusted under 35 U.S.C. 154(b) by 378 days.

(21) Appl. No.: 17/588,143

(22) Filed: Jan. 28, 2022

(65) Prior Publication Data

US 2023/0240747 A1 Aug. 3, 2023

(51) Int. Cl.
*A61B 18/20* (2006.01)
*A61B 18/00* (2006.01)

(52) U.S. Cl.
CPC .... *A61B 18/203* (2013.01); *A61B 2018/0047* (2013.01); *A61B 2018/00577* (2013.01); *A61B 2018/00589* (2013.01); *A61B 2018/00696* (2013.01); *A61B 2018/00702* (2013.01); *A61B 2018/00761* (2013.01); *A61B 2018/00982* (2013.01)

(58) Field of Classification Search
CPC .......... A61B 18/203; A61B 2018/0047; A61B 2018/00577; A61B 2018/00589; A61B 2018/00696; A61B 2018/00702; A61B 2018/00761; A61B 2018/00982; A61B 2018/205547; A61B 2018/00452; A61B 2018/20353; A61N 5/0616; A61N 5/067; A61N 2005/0626

See application file for complete search history.

(56) References Cited

U.S. PATENT DOCUMENTS

| | | |
|---|---|---|
| 2005/0143719 A1 | 6/2005 | Sink |
| 2008/0294150 A1 | 11/2008 | Altshuler et al. |
| 2011/0230870 A1 | 9/2011 | Moy |
| 2012/0065551 A1 | 3/2012 | Aviad et al. |

OTHER PUBLICATIONS

European Application 23 15 3400 Extended European Search Report dtd Jun. 5, 2023; 7 pages.

*Primary Examiner* — Scott M. Getzow
(74) *Attorney, Agent, or Firm* — Haynes and Boone, LLP (57) ABSTRACT

A laser system for fractional injury is provided that varies the amount of energy provided per each pulse to provide a series of first pulses each having a first energy and to provide a series of second pulses each having a second energy that is less than the first energy. A scanner distributes the series of first pulses across an area of tissue to be fractionally injured according to a first pitch and distributes the series of second pulses across the area of tissue to be fractionally injured according to a first pitch that is less than the first pitch.

17 Claims, 6 Drawing Sheets

FIG. 5 pulsing a laser to provide a series of first pulses and a series of second pulses so that an energy delivered by each first pulse is greater than an energy delivered by an energy of each second pulse — 600 scanning the series of first pulses and the second series of pulses across an area of tissue to be fractionally injured so that a first pitch separates adjacent ones of the first pulses and so that a second pitch separate adjacent ones of the second pulses, wherein the second pitch is less than the first pitch — 605

FIG. 6

THREE-DIMENSIONAL LASER SCAN FOR FRACTIONAL INJURY

TECHNICAL FIELD

This application relates to lasers for fractional injury, and more particularly to a three-dimensional laser scan for fractional injury.

BACKGROUND

In a traditional laser ablative resurfacing of the skin, the laser ablates the entirety of skin surface being treated. For example, a scan or uneven pigmentation may be ablated in this fashion. Since the laser is ablating the entire upper surface of the skin (the epidermis) being treated, a laser resurfacing may also be denoted as a laser peel. The injury to the upper skin layers triggers the underlying dermis to develop more collagen and thus cause beneficial tightening to address wrinkles and sagging such as caused by aging. But the cosmetic benefits of a laser peel are also associated with risks of infection, increased healing time, and scarring.

To provide the benefits of a laser peel but with reduced risks, fractional dermal ablation (which may also be denoted as fractional laser resurfacing) was developed. As implied by the "fractional" designation, a fractional dermal ablation does not ablate the entire epidermis of a treatment area. Instead, the laser is pulsed while scanning to form ablated columns of skin that are separated by healthy tissue. The presence of healthy, undamaged skin about each ablated column speeds healing and reduces the risk of infection. But the resulting damage to the dermis in each column of ablated tissue stimulates the growth and reorganization of collagen, which provides a beneficial rejuvenation of the skin.

As laser technology has been advanced, the diameter or width of the laser beam that is pulsed and scanned in fractional laser treatments has shrunk into the micron regime (e.g., 50 to 100's of microns). Such enhanced fractional laser treatments may be denoted as micro fractional ablation. To speed healing and reduce the risks of infection, a micro fractional ablation should only ablate a certain percentage of the skin surface. The relationship between the treated or ablated portion of the skin and the surrounding undamaged skin may be denoted as the scan density. Should the scan density be increased above a threshold level, the patient may be exposed to an unnecessary risk of infection and lengthy healing times. But as the scan density is decreased, the skin rejuvenation may not be sufficient.

Micro laser ablation is one form of fractional injury. Fractional injury may also be produced by non-ablative lasers such as for coagulation, tissue necrosis, and non-immediately destructive tissue heating. Fractional injury thus suffers from an unresolved tension between achieving sufficient fractional injury and keeping the scan density at safe levels.

SUMMARY

In accordance with a first aspect of the disclosure, a laser system for fractional injury is provided that includes: a laser energy controller configured to control a series of first laser pulses and a series of second laser pulses so that an energy delivered by each first laser pulse is greater than an energy delivered by each second laser pulse; and a scanner configured to control a placement of the series of first laser pulses across an area of tissue to be fractionally injured so that adjacent ones of the first laser pulses are separated by at least a first pitch and to control the control a placement of the series of second laser pulses across the area of tissue to be fractionally injured so that adjacent ones of the second laser pulses are separated by at least a second pitch that is less than the first pitch.

In accordance with a second aspect of the disclosure, a method of laser fractional injury is provided that includes: pulsing a laser to provide a series of first pulses and a series of second pulses so that an energy delivered by each first pulse is greater than an energy delivered by an energy of each second pulse; and scanning the series of first pulses and the second series of pulses across an area of tissue to be fractionally injured so that a first pitch separates adjacent ones of the first pulses and so that a second pitch separate adjacent ones of the second pulses, wherein the second pitch is less than the first pitch.

These and other advantageous features may be better appreciated through the following detailed description.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

Laser fractional injury covers a wide variety of tissue injury. For example, if the tissue being fractionally injured by a pulsing of a laser is heated to 100° C. or greater, the resulting fractional injury is typically denoted as being ablative. If the tissue being fractionally injured by the pulsing of the laser is not heated to 100° C. or greater, the resulting fractional injury is commonly denoted as being non-ablative. There are various forms of non-ablative fractional injury. For example, if the tissue being fractionally injured is heated to greater than 70° C. but less than 100° C., the fractional injury is commonly denoted as a fractional coagulation or tissue necrosis. Should the pulsing of the laser instead heat the tissue being fractionally injured to less than 70° C. but above 40° C., the fractional injury is often denoted as non-immediately destructive tissue heating.

Regardless of whether a fractional injury is ablative or not, there is a tension between achieving sufficient fractional injury and keeping the scan density at acceptable levels. To resolve this tension, a three-dimensional (3D) laser scan pattern for fractional injury is provided. The following discussion will address a fractional injury scan of the skin, but it will be appreciated that the 3D laser scan pattern disclosed herein is also applicable to both ablative and non-ablative fractional injury of other types of tissues than just skin. In a 3D scan, the heat delivered per pulse defines a plurality of pulse classes. Each pulse in a given class delivers the same amount of heat. It is a design choice as to how many classes of pulses a given 3D scan will include. In the following discussion it will be assumed that three classes are used without loss of generality. For example, a first class of pulses delivers more heat per pulse than the heat per pulse delivered by a second class of pulses. In turn, the second class of pulses provide a greater heat per pulse than a third class of pulses, and so on.

The heat delivered by each pulse may be defined by the energy (e.g., a total number of joules) delivered to the portion of skin being energized by the pulse. Alternatively, the energy delivered per area of skin being illuminated by the laser pulse (e.g., joules per cm2) may characterize the heat delivered by each pulse. With respect to delivering a given amount of energy (and thus heat), the pulse duration may be the same whereas the laser intensity or power is varied from one class of pulses to another. Alternatively, the laser power may be constant for each pulse, but the pulse duration varied from one class of pulses to another to control the amount of heat being delivered.

The spacing between pulses in each class is proportional to the heat delivered per pulse for the class. For example, with respect to the three classes of pulses discussed above, the first class has the greatest heat per pulse whereas the second class has more heat per pulse than the third class of pulses. If there are just three classes of pulses, the third class thus delivers the least amount of heat per pulse. Given these relative amounts of heat per pulse, the first class of pulses has a first pitch or spacing between adjacent pulses. The second class of pulses is similarly positioned to have a second pitch or spacing between adjacent pulses that is less than the first pitch. Finally, each pulse in the third class of pulses is positioned according to a third pitch that is less than the second pitch (and hence less than the first pitch).

The varied pitch for the classes of pulses leads to a "two-dimensional" nature to the scan since the skin may be deemed to form a plane defined by two dimensions. But there is a third dimension to the scan because of the varied depths of fractional injury provided by the pulse classes. For example, the first class of pulses are most energetic. In the case of an ablative dermal scan, the first class of pulses will thus ablate most deeply into the skin. The second classes of pulses have less energy and thus produce a fractional injury that does not extend as deeply into the tissue being treated. For example, in the case of an ablative dermal scan, the second class of pulses will not ablate as deeply into the skin as compared to the first class of pulses. The third class of pulses has even less energy than the second class of pulses. The third class of pulses will thus ablate more shallowly as compared to the other classes in an ablative 3D laser scan. If the skin surface is deemed to be defined by the X and Y axes in a Cartesian coordinate system, the varied fractional injury depth would be defined by the Z axis. The resulting three-dimensionality provides sufficient fractional injury without the risk of heat injury that would result from traditional laser scans. To provide a better appreciation of this advantageous feature, some traditional two-dimensional scan patterns will be discussed first, followed by a discussion of an example three-dimensional scan pattern.

Figure 1:
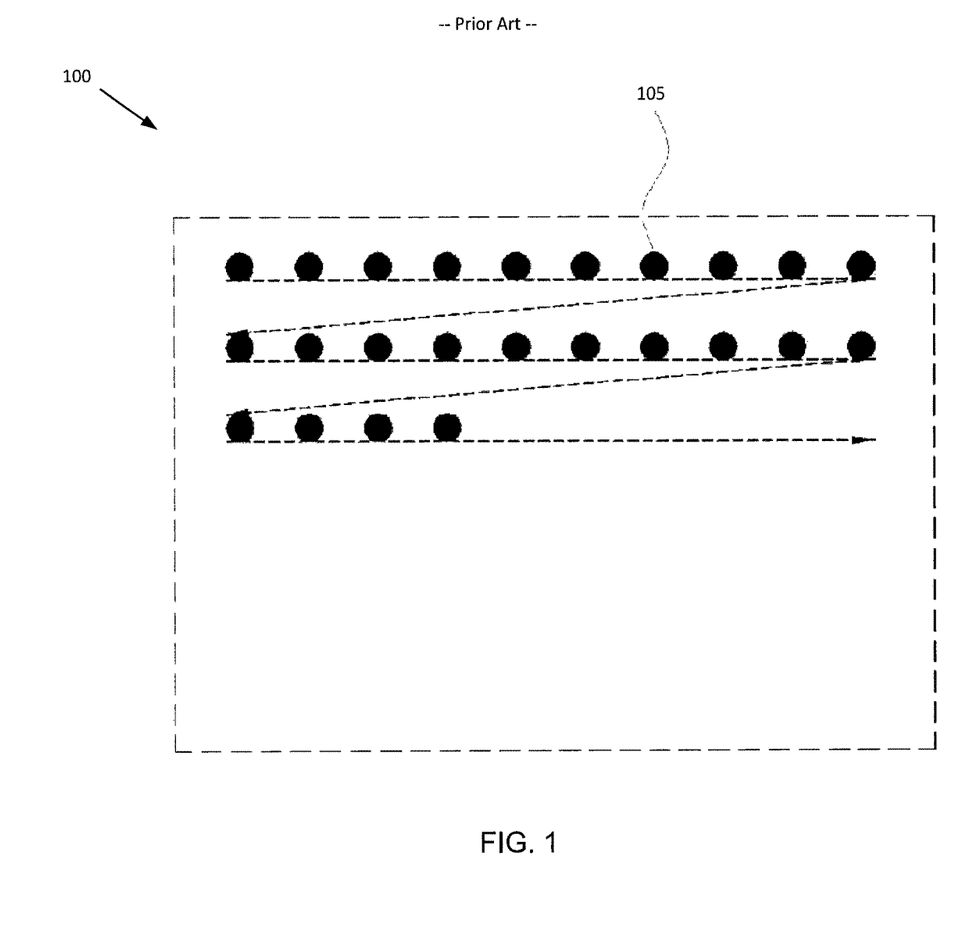
FIG. 1 illustrates a traditional two-dimensional laser scan raster pattern.
Figure 2:
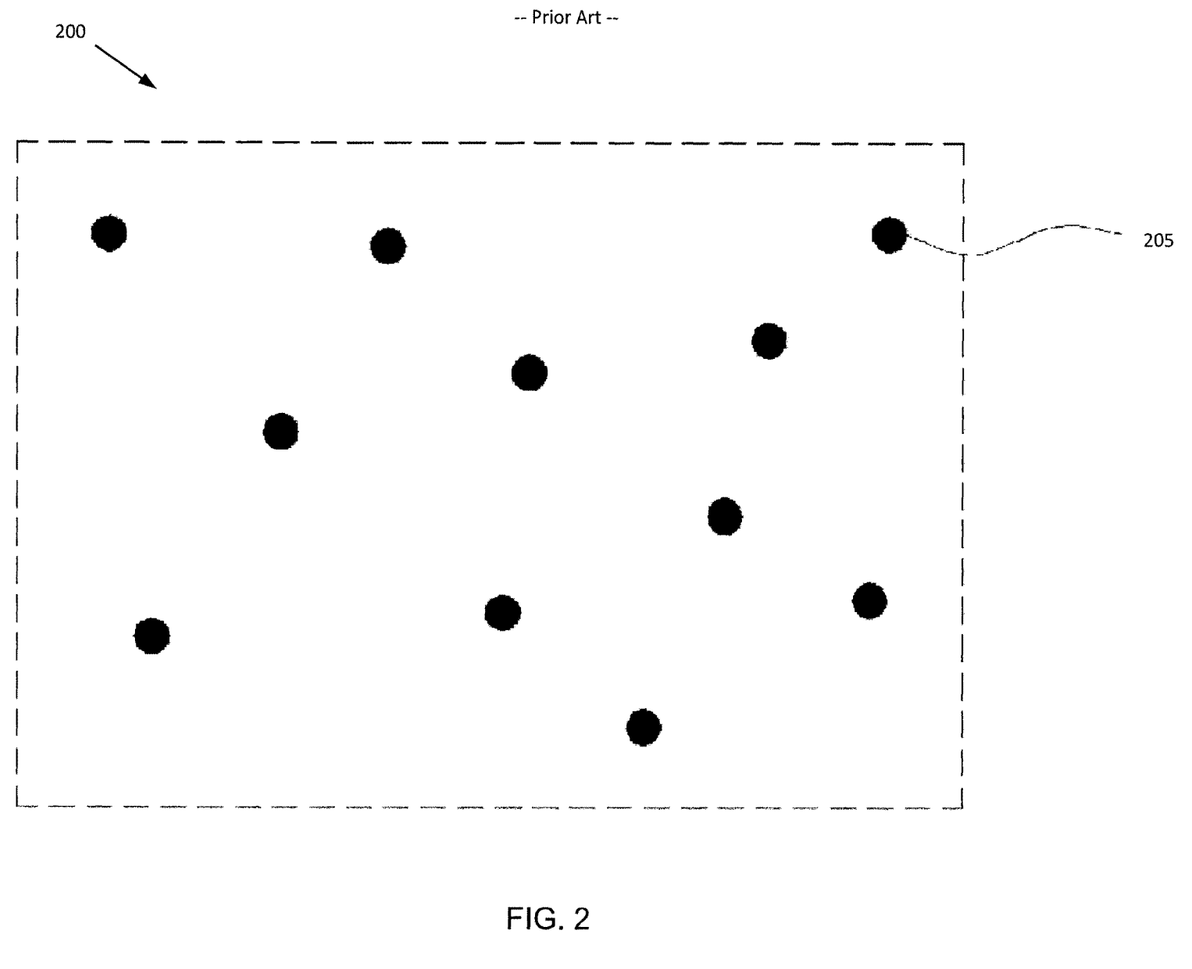
FIG. 2 illustrates a traditional two-dimensional laser scan random pattern.

A linear two-dimensional scan pattern 100 is shown in FIG. 1. Each laser scan spot 105 is separated according to a regular pitch and arranged in linear rows and columns akin to a raster scan in a display. Because the linear nature of such a scan leads to facial injury having unnatural straight lines, a random two-dimensional scan pattern 200 was developed as shown in FIG. 2. The spacing between each laser scan spot 205 is irregular and thus leads to a more natural appearing injury edge as the spots 205 are not aligned according to linear rows and columns. However, both scan 100 and scan 200 suffer from the tension discussed earlier between achieving sufficient ablation and the risks of excessive heat delivery. For example, suppose that a relatively large amount of heat is delivered for each laser scan spot 105 of scan 100. As the pitch is reduced, tissue that was heated due to one laser scan spot 105 may be re-heated by an adjacent laser scan spot 105. The pitch must thus be maintained to be relatively large, which reduces the scan density. Similarly, the energy delivered by each laser scan spot 205 must take into account the minimum pitch in the irregular spacing of scan 200. Should the energy be too large, adjacent scan spots 205 will merge, which then destroys the desired surrounding of each ablated column of skin tissue with healthy tissue.

Figure 3:
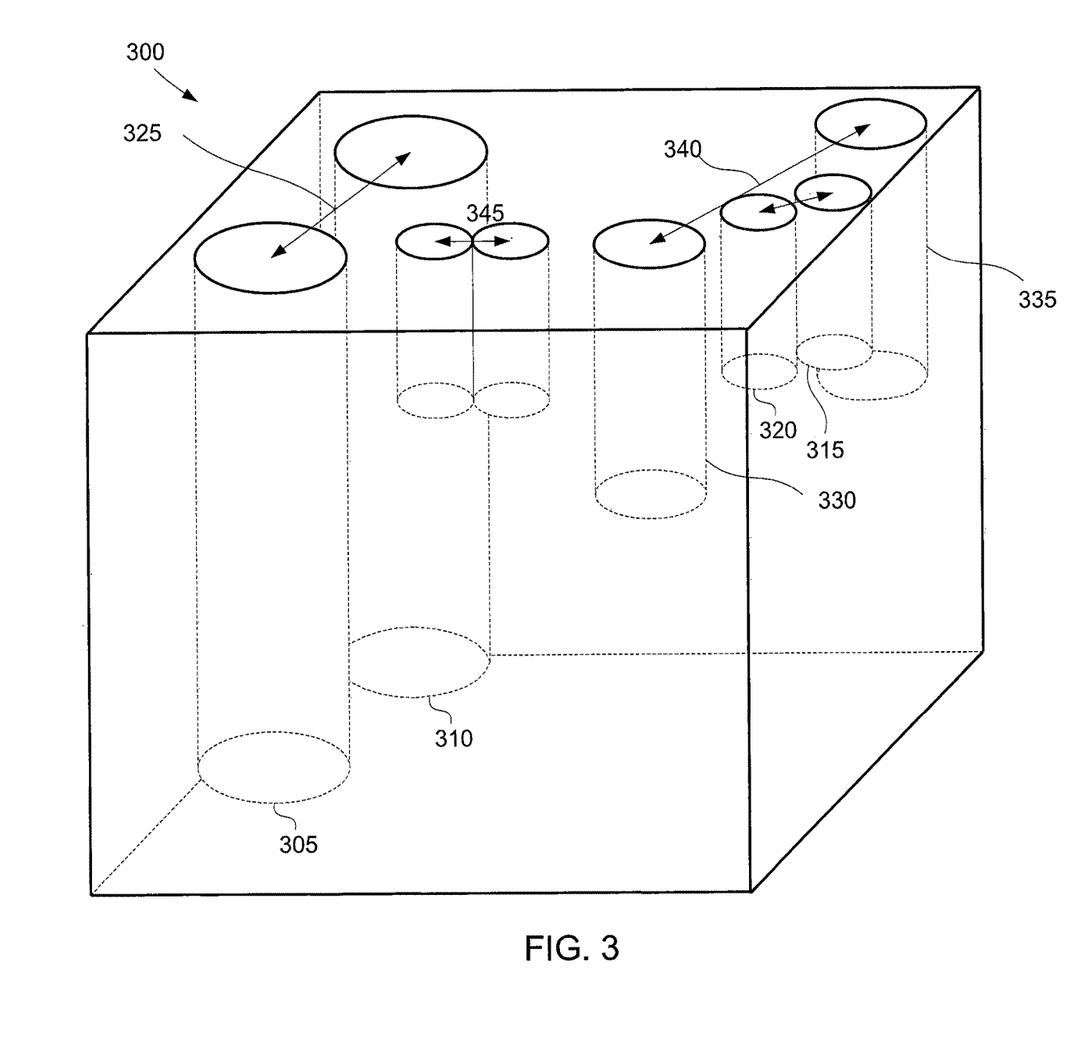
FIG. 3 illustrates a three-dimensional laser scan pattern in accordance with an aspect of the disclosure.

In sharp contrast, a three-dimensional laser scan pattern 300 such as shown in FIG. 3 achieves sufficient fractional injury without the risk of excessive heat. A three-dimensional scan uses at least two classes of laser pulses. In scan pattern 300, three classes are used as discussed earlier. Pulses 305 and 310 are examples of a first class of pulses having a relatively large energy. The first class of pulses are also denoted herein as a series of first pulses. The large amount of energy per each first pulse provides a deep fractional injury column to stimulate regrowth of collagen in the dermis, but this significant fractional injury also delivers a relatively large amount of heat to the skin tissue. To limit excessive heating of tissues from adjacent pulses, adjacent first pulses such as pulses 305 and 310 are separated by a first pitch or separation 325 that is relatively large.

In contrast, a pair of adjacent pulses 330 and 335 in a second class of pulses are separated by a second pitch or separation 340. The second class of pulses are also denoted herein as a series of second pulses. Because the energy per pulse is reduced for the second class of pulses as compared to the energy per pulse of the first class, each second pulse does not fractionally injure the tissue being treated as deeply and delivers less heat as compared to the first pulses. Due to this reduced amount of heat, second pitch 340 is smaller that first pitch 325. In this fashion, the second class of pulses increase the scan density as compared to what would otherwise be possible if only the first class of pulses were used.

A pair of adjacent pulses 320 and 315 are examples of a third class of pulses having a reduced amount of energy per pulse as compared to the second class of pulses. The third class of pulses is also denoted herein as a series of third pulses. Each third pulse thus delivers the least amount of heat per pulse. The depth of the fractional injury from pulses 320 and 315 is thus smaller than that produced by pulses 330 and 335. Due to this reduced amount of heat delivered per pulse, adjacent third pulses such as pulses 320 and 315 are separated by a third pitch 345 that is less than second pitch 340 (and thus less than first pitch 325). Due to the reduced pitch, the third class of pulses increases the scan density as compared to what would be possible if only the first and second classes of pulses were used.

Figure 4:
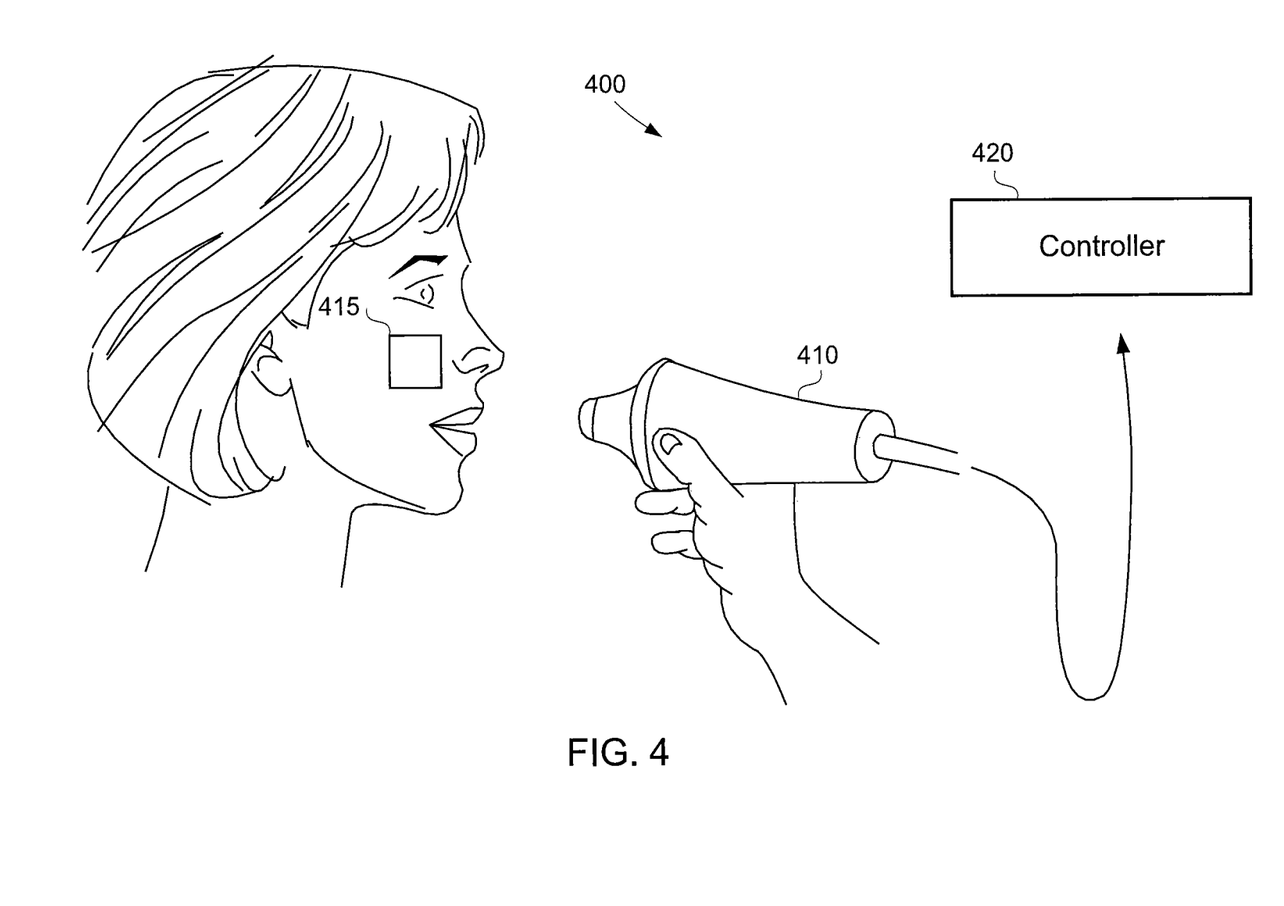
FIG. 4 illustrates a system for the three-dimensional fractional laser injury of the skin of a patient in accordance with an aspect of the disclosure.

An example system 400 for a three-dimensional laser fractional injury of the skin of a patient is shown in FIG. 4. A clinician positions a laser hand piece 410 to perform a laser scan of a skin portion 415. A controller 420 controls a scanner (discussed further herein) that scans the laser beam to scan the appropriate laser pulses across skin portion 415. At the same time, controller 420 controls the scan energy for each laser pulse to produce the desired number of laser pulses of each class within skin portion 415. With skin portion 415 ablated, the user may then reposition laser hand piece 410 to begin a three-dimensional laser fractional injury of another skin portion. The laser scan and repositioning of the laser hand piece 410 is then repeated until all the skin portions to be treated are completed.

Figure 5:
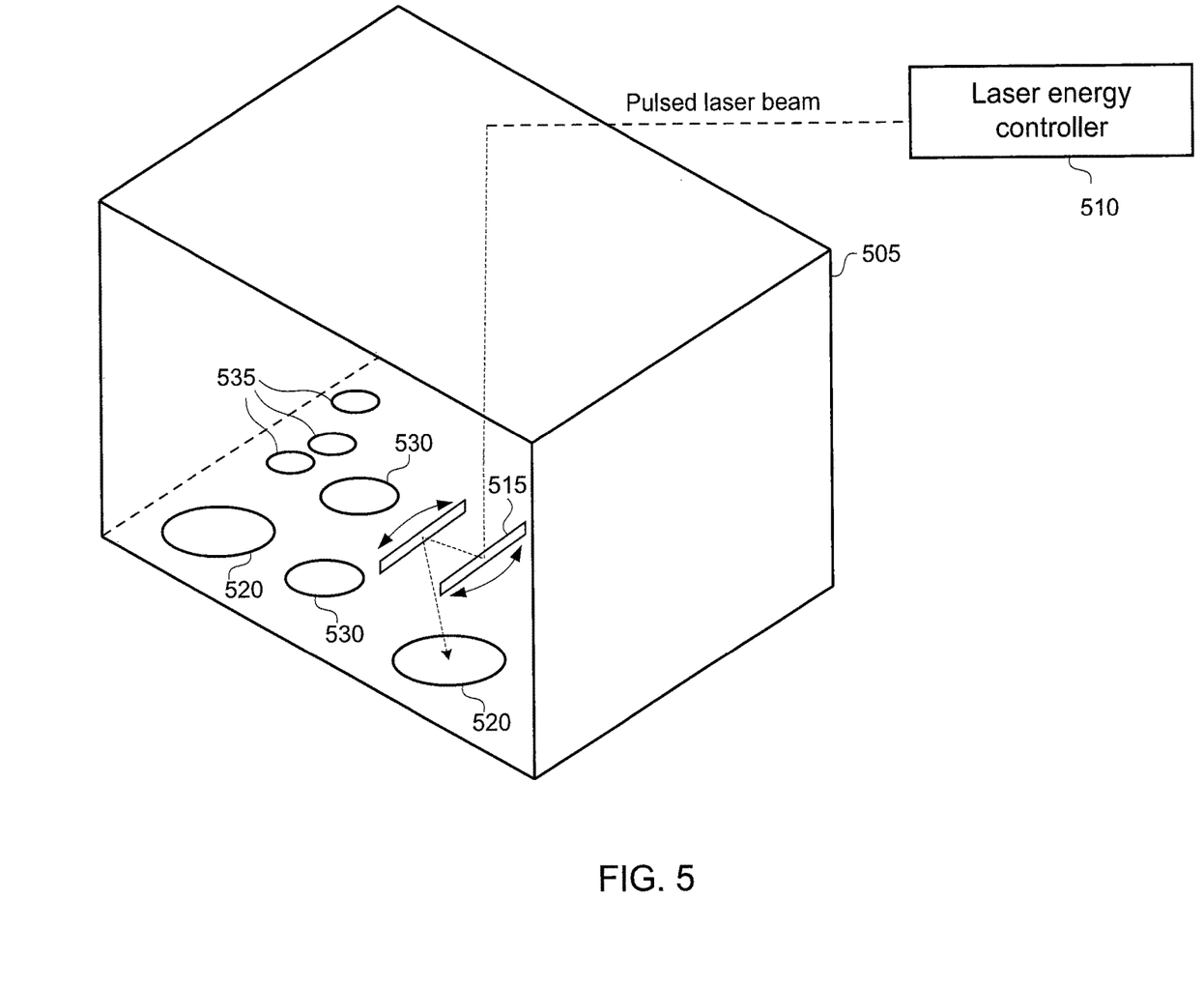
FIG. 5 illustrates a distal end of the laser hand piece in the system of FIG. 4 in accordance with an aspect of the disclosure.

A distal portion 505 of an example laser hand piece is shown in FIG. 5. A scanner 515 such as set of mirrors are controlled by controller 405 (FIG. 4) to position the classes of laser pulses across a skin portion according to their respective pitches. The first class of pulses are represented by pulses 520. Controller 405 includes a laser energy controller 510 that controls the amount of energy delivered by the pulses in each class. For example, laser energy controller 510 may control the pulse duration and/or the power of the laser beam for each pulse to control the amount of energy per pulse. A pair of pulses 530 are second class pulses whereas a triplet of pulses 535 are third class pulses.

The sequencing of the various classes of pulses may be based upon the heat energy being delivered per pulse. For example, suppose an area of tissue was to be fractionally injured with fifty first pulses, one-hundred second pulses, and two-hundred third pulses. It would be relatively slow to first pulse all the pulses in one class of pulses, then all the pulses in another class of pulses, and so on. To provide a faster scanning, a sequence such as 1-3-3-2-3-3-2 may sequentially repeated, wherein the 1 represents a pulse of the first class, a 2 represents a pulse of the second class, and a 3 represents a pulse of the third class. Given the energy of the initial first pulse in such a sequence, the subsequent pair of third class pulses need a certain spacing or pitch from the initial pulse. Similarly, the energy of the first second class pulse requires a certain spacing from the just ablated third class pulses, and so on. There is thus a temporal aspect to the spacing of the various pulses that takes into account the heat delivered by preceding pulses.

The pitch between adjacent first pulses may vary depending upon the energy per pulse in the first class of pulses. The following Table 1 for the first class of laser pulses gives some example depths in millimeters for the fractionally injured column of tissue that results from each pulse, the milli-Joules of energy being delivered by each pulse, the radius of each column (MTZ) in microns, the pitch in millimeters, and the resulting scan density:

TABLE 1

| Depth | mJ | MTZ | Pitch | Density |
| --- | --- | --- | --- | --- |
| 0.75 | 50 | 300 | 0.75 | 40% |
| 1 | 60 | 315 | 1 | 32% |
| 1.5 | 90 | 350 | 1.5 | 23% |

The following Table 2 is analogous to Table 1, but is directed to the second class of laser pulses:

TABLE 2

| Depth | mJ | MTZ | Pitch | Density |
| --- | --- | --- | --- | --- |
| 0.35 | 10 | 150 | 0.35 | 43% |
| 0.45 | 16 | 200 | 0.45 | 44% |
| 0.55 | 26 | 250 | 0.55 | 45% |

Similarly, the following Table 3 is also analogous to Table 1, but is directed to the third class of pulses:

TABLE 3

| Depth | mJ | MTZ | Pitch | Density |
| --- | --- | --- | --- | --- |
| 0.15 | 2 | 150 | 0.15 | 100% |
| 0.2 | 4 | 150 | 0.2 | 75% |
| 0.25 | 6 | 150 | 0.25 | 60% |

Figure 6:
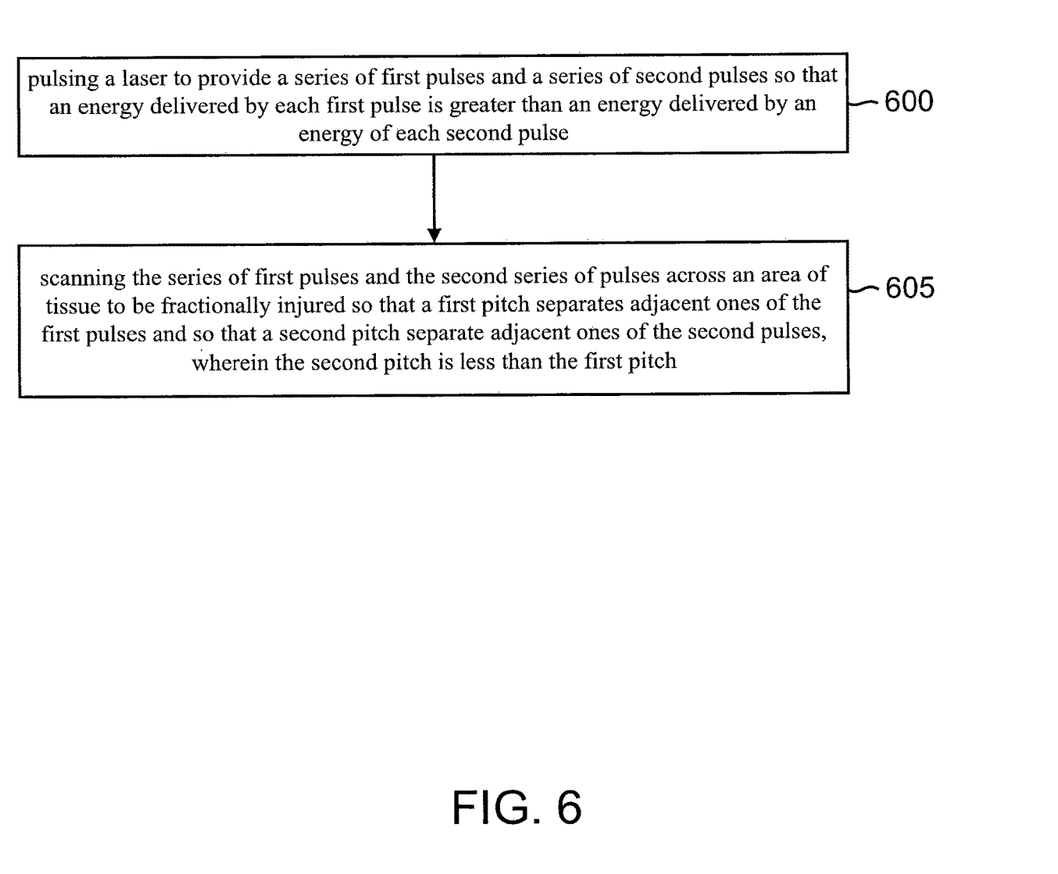
FIG. 6 is a flowchart for an example method of laser fractional injury in accordance with an aspect of the disclosure.

An example method of laser fractional injury will now be discussed with respect to the flowchart of FIG. 6. The method includes an act 600 of pulsing a laser to provide a series of first pulses and a series of second pulses so that an energy delivered by each first pulse is greater than an energy delivered by an energy of each second pulse. Pulses 520 or pulses 305 and 310 are an example of the first series of pulses. In addition, the method includes an act 605 of scanning the series of first pulses and the second series of pulses across an area of tissue to be fractionally injured so that a first pitch separates adjacent ones of the first pulses and so that a second pitch separate adjacent ones of the second pulses, wherein the second pitch is less than the first pitch. Pulses 330 and 335 or pulses 530 is an example of the series of second pulses.

Those of some skill in this art will by now appreciate and depending on the particular application at hand, many modifications, substitutions and variations can be made in and to the materials, apparatus, configurations and methods of use of the devices of the present disclosure without departing from the scope thereof. In light of this, the scope of the present disclosure should not be limited to that of the particular embodiments illustrated and described herein, as they are merely by way of some examples thereof, but rather, should be fully commensurate with that of the claims appended hereafter and their functional equivalents.

I claim:

1. A laser system for fractional injury, comprising:
a laser energy controller configured to control a series of first laser pulses and a series of second laser pulses so that an energy delivered by each first laser pulse is greater than an energy delivered by each second laser pulse; and
a scanner configured to control a placement of the series of first laser pulses across an area of tissue to be fractionally injured so that adjacent ones of the first laser pulses are separated by at least a first pitch and to control the control a placement of the series of second laser pulses across the area of tissue to be fractionally injured so that adjacent ones of the second laser pulses are separated by at least a second pitch that is less than the first pitch,
wherein the laser energy controller is further configured to control the energy of each first laser pulse so as to ablate a column of skin tissue having a first depth and a first diameter and to control the energy of each second laser pulse so as to ablate a column of skin tissue having a second depth and a second diameter, and wherein the first depth is greater than the second depth and the first diameter is greater than the second diameter.

2. The laser system of claim 1, wherein the laser energy controller is further configured to control a series of third laser pulses so that an energy delivered by each third laser pulse is less than the energy delivered by each second laser pulse, and wherein the scanner is further configured to control a placement of the series of third laser pulses across the area of tissue to be fractionally injured so that adjacent ones of the third laser pulses are separated by at least a third pitch that is less than the second pitch.

3. The laser system of claim 2, wherein the scanner includes a plurality of mirrors.

4. The laser system of claim 2, wherein the laser system is a laser system for fractional dermal ablation, and wherein the area of tissue to be ablated is an area of skin tissue.

5. The laser system of claim 4, wherein the laser energy controller is further configured to control a duration of each first pulse to be longer than a duration of each second pulse.

6. The laser system of claim 4, wherein the laser energy controller is further configured to sequence the series of first pulses, the series of second pulses, and the series of third pulses so that each first pulse is followed by at least one second pulse and by at least one third pulse.

7. The laser system of claim 2, wherein the laser system is a non-ablative laser system, and wherein the area of tissue to be non-ablatively fractionally injured is an area of skin tissue.

8. A method of laser fractional injury, comprising:
pulsing a laser to provide a series of first pulses and a series of second pulses so that an energy delivered by each first pulse is greater than an energy delivered by an energy of each second pulse and so that each first laser pulse ablates a column of skin having a first depth and a first diameter and so that each second laser pulse ablates a column of skin having a second depth and a second diameter, and wherein the first depth is greater than the second depth and the first diameter is greater than the second diameter; and
scanning the series of first pulses and the second series of pulses across an area of tissue to be fractionally injured so that a first pitch separates adjacent ones of the first pulses and so that a second pitch separate adjacent ones of the second pulses, wherein the second pitch is less than the first pitch.

9. The method of claim 8, further comprising:
pulsing the laser to provide a series of third pules so that an energy delivered by each third pulse is greater than the energy delivered by each second pulse; and
scanning the series of third pulses across the area of tissue to be fractionally injured so that a third pitch separates adjacent ones of the third pulses, wherein the third pitch is less than the second pitch.

10. The method of claim 9, wherein pulsing the laser is sequenced so that each first pulse is followed by at least one second pulse.

11. The method of claim 10, wherein pulsing the laser is further sequenced so that each second pulse is followed by at least one third pulse.

12. The method of claim 9, wherein the scanning of the area of tissue to be fractionally injured comprises scanning an area of skin on a face of a patient.

13. The method of claim 9, further comprising:
controlling a duration of each first pulse to be longer than a duration of each second pulse.

14. The method of claim 13, further comprising:
controlling a duration of each third pulse to be shorter than the duration of each second pulse.

15. The method of claim 9, further comprising:
controlling a power of the laser for each first pulse to be greater that a power of the laser beam for each second pulse.

16. The method of claim 15, further comprising:
controlling a power of the laser for each third pulse to be less than the power of the laser for each second pulse.

17. The method of claim 8, wherein scanning the series of first pulses and the series of second pulses comprises controlling a plurality of mirrors.

* * * * *